(12) United States Patent
Vyden

(10) Patent No.: US 6,503,953 B2
(45) Date of Patent: Jan. 7, 2003

(54) METHODS FOR TREATING ATOPIC DISORDERS

(75) Inventor: John K. Vyden, Beverly Hills, CA (US)

(73) Assignee: Atopic Pty Ltd., Sydney (AU)

(*) Notice: Subject to any disclaimer, the term of this patent is extended or adjusted under 35 U.S.C. 154(b) by 0 days.

(21) Appl. No.: 09/916,962

(22) Filed: Jul. 26, 2001

(65) Prior Publication Data

US 2002/0106342 A1 Aug. 8, 2002

Related U.S. Application Data

(60) Provisional application No. 60/220,916, filed on Jul. 26, 2000.

(51) Int. Cl.$^7$ .............................................. A61K 31/04
(52) U.S. Cl. ....................................... 514/741; 514/826
(58) Field of Search ................................ 514/741, 826

(56) References Cited

U.S. PATENT DOCUMENTS

| | | | |
|---|---|---|---|
| 4,874,850 A | * 10/1989 | Paradies | 536/3 |
| 5,637,314 A | * 6/1997 | Sharpe et al. | 424/423 |
| 5,703,088 A | * 12/1997 | Sharpe et al. | 514/278 |
| 5,900,257 A | 5/1999 | Breton et al. | 424/639 |
| 5,958,432 A | 9/1999 | Breton et al. | 424/401 |
| 5,993,787 A | 11/1999 | Sun et al. | 424/59 |
| 6,028,063 A | 2/2000 | Kruse et al. | 514/91 |
| 6,048,855 A | 4/2000 | De Lacharriere et al. | 514/213 |
| 6,207,703 B1 | * 3/2001 | Ponikau | 514/254.07 |
| 6,291,500 B2 | * 9/2001 | Ponikau | 514/282 |
| 6,391,282 B1 | * 5/2002 | Dugger, III | 424/400 |

OTHER PUBLICATIONS

Database: Google.com., "Hand Eczema", Novartis Pharmaceuticals Corp. 1998 National Eczema Association for Science and Education, total 5 pages, see especially p. 3/5.*
Database: Google.com., "Atopic Dermatitis: A review of Diagnosis and Treatment", Correale et al., Sep. 15, 1999. 10 pages.*
Database Caplus, AN:1987:201534, Okamoto et al., "Percitaneous absorption and skin sensitization", abstract, 1986, vol. 12, pp. 159–168.*
Database Caplus, AN:1994:2358, Jaskilecki et al., "Barrier properties of silicone cream in protection against sensitizing . . . .", abstract, 1992, vol. 25(4), pp. 383–386.*

* cited by examiner

Primary Examiner—Ray Henley
Assistant Examiner—Vickie Kim
(74) Attorney, Agent, or Firm—Christie, Parker & Hale, LLP

(57) ABSTRACT

A method for treating an atopic disorder in a patient is provided. The method comprises administering to the patient an effective amount of at least one of an antifungal and an antibiotic over a period of time. The method further comprises reducing over the period of time the application of emollients to the patient by at least about 50%, relative to the amount of application of emollients prior to treatment.

46 Claims, 8 Drawing Sheets

(8 of 8 Drawing Sheet(s) Filed in Color)

METHODS FOR TREATING ATOPIC DISORDERS

CROSS-REFERENCE TO RELATED APPLICATION

This application claims priority of U.S. Provisional Application No. 60/220,916, filed Jul. 26, 2000, the entire disclosure of which is incorporated herein by reference.

FIELD OF THE INVENTION

The present invention is directed to methods for treating atopic disorders, including asthma, eczema, sinusitis, bronchitis, and allergic rhinitis.

BACKGROUND

In the United States and other Western countries, the reported incidence of asthma is about 4–5% of the population. About half the cases develop before the age of ten and another third before the age of forty. The cost of treating asthma is enormous. Emergency room visits approximate two million a year and hospitalizations, about 500,000. Total cost of medication is estimated at one billion dollars a year, while the loss of productivity within the families of children is perhaps another billion dollars a year. The number of asthma prescriptions is thought to double per decade. In the United Kingdom, the cost of asthma treatment represented 11% of the national health budget.

The physiological hallmark of asthma is a reversible obstruction in the airways brought about by vascular congestion, thick tenacious secretions, bronchial wall edema, and smooth muscle contractions. During an attack, there is a compromise of lung function. Asthma is a chronic inflammatory disease of uncertain cause. A noticeable therapeutic change is the increased use of corticosteroids in its management.

The United Kingdom has one of the highest rates of asthma per capita of anywhere in the world. The jet stream flowing across the Atlantic keeps the British Isles wet, damp, and humid. They have an advanced "westernized" society and since dampness makes mildew grow, one sees a high incidence of asthma.

The United States, also a "western" society, has diversified weather due to its greater size. For instance, a large part of the western United States is desert. Denver and Arizona have two of the lowest areas of humidity and asthma. Asthmatics frequently move to these areas, particularly Arizona, because the extreme heat and low humidity dry dampness kill mildew and improve asthma.

In Sweden, high indoor humidity is associated with increased asthma. (See Aberg N. Asthma and Allergic rhinitis in Swedish conscripts. Clin Exp Allergy 1989;19:59–63; and Wickman M, Nordvall S L, Pershagen G. Risk factors in early childhood for sensitization to airborne allergens. Pediatr Allergy Immunol 1992;3:128–33.) Increases in asthma and allergic diseases are related to an increasingly unventilated environment. (See Aberg N, Hesselmar B, Aberg B, Eriksson B. Increase of asthma, allergic rhinitis and eczema in Swedish school children between 1979 and 1991. Clin and Experimental Allergy 1995;25:815–819.) High indoor humidity and houses damaged by dampness, owing to poor ventilation, are related to a high frequency of allergic symptoms. (See Andrae S, Axelson O, Bjorksten B, Frediksson M, Kjellman -IM. Symptoms of bronchial hyperreactvity and asthma in relation to environmental factors. Arch Dis Child 1988;63:473–8.) Environmental exposure early in life also seems important. (See Bjorksten B. Risk factors in early childhood for the development of atopic diseases. Allergy 1994;49:400–7; and Aberg N. Birth season variation in asthma and allergic rhinitis. Clin Exp Allergy 1989;19:643–8.) Dampness in homes expressed as moisture inside windowpanes, and as a noticeable dampness or mildew in the home, increased the risk of asthma, rhinitis and eczema, as well as a history of upper respiratory infections. There is a dose response relationship between the amount of moisture inside the Windows and risk. The highest risk from dampness exposure is in the first year of life.

A risk factor in allergic diseases is a parental history of allergic disease. About twice as many children have allergic disease if one parent was ever afflicted, and three times as many if both parents were afflicted, as compared with cases with no parental history (p<0.001). If parents smoked during the first year of life, it did not increase the risk for development of an allergic disease, not even asthma of the worst severity. The frequency of upper respiratory infections and dampness in the homes were additive, but not synergistic.

Some researchers suggested that indoor air quality and factors of a chemical or microbiological nature related to damp homes are important to the pathogenesis of allergic disease. (See Aberg N, Sundell J, Eriksson B, Hesselmar B, Aberg B. Prevalence of allergic diseases in school children in relation to family history, upper respiratory infections and residential characteristics. Allergy 1996;51 :232–237.) They also found that high indoor air humidity and dampness were strong risk factors underlying all allergic disease. Inhaled fungus seems able to cause further sensitization with resultant symptoms. High indoor air humidity and dampness might encourage fungus growth on skin and in the upper or lower respiratory tracts. He also found that recent repainting and repairing of a child's bedroom moderately increased risk of allergic disease. Repairing and repainting of bedroom walls are notorious for exposing underlying dampness and mildew and releasing it into the bedroom environment. Finnish workers reported evidence between, and association with, mold or mildew problems in school buildings and the presence of manifest and occult asthma in the pupils. (See Taskinen T, Meklin T, Nousiainen M, Husman, T, Nevalainen A, Korppi M. Moisture and mold problems in schools and respiratory manifestations in school children: clinical and skin test findings. Acta Paediatr 1997;86:1181–7.)

Yemaneberhan, et al., working in Ethiopia, believe that the asthma and allergy being seen in developing countries may be associated with the adoption of a "western" lifestyle. (See Yemaneberhan H, Bekele Z, Venn A, Lewis S, Parry E, Britton J. Prevalence of wheeze and asthma and relation to atopy in urban and rural Ethiopia. The Lancet 1997;350:85–90.) This group found that wheeze and asthma are especially rare in the rural subsistence areas of Ethiopia where there is a reduced prevalence of these symptoms in this environment. In Jimma, which is partly westernized, self-reported asthma emerged as a clinical problem about ten years before their studies began, which is consistent with an effect of new environmental exposures. Although they could not identify the factor leading to increases in asthma and allergy, general changes in the domestic environment are likely to be involved.

Furthermore, Esamai and Anabwani found in Kenya that the prevalence of wheezing, rhinitis, and itchy rashes were similar to previous studies in Estonia. (See Esamai F, Anabwani G M. Prevalence of asthma, allergic rhinitis and dermatitis in primary school children in Uasin Gishu district, Kenya. East Afr Med J 1996;73(7):474–478.) The prevalence of asthma and allergic diseases are increasing worldwide, and it is more so in developing countries, which rapidly raise the living standard of parts of their population.

Trepka et al. studied the epidemiology of asthma, rhinitis and atopic dermatitis in Eastern versus Western populations. They found that the rate of physician diagnosed asthma and rhinitis were higher in Western Germany, though there was a tendency for slightly less atopic dermatitis in children. They speculated that if lifestyle and environmental factors play a role in this process, then the incidence of disease should converge, as the two societies become more similar. (See Trepka M J, Heinrich J, Wichmann H E. The epidemiology of atopic diseases in Germany: an east-west comparison. Rev Environmental Health 1996;11(3): 119–31.)

Hong Kong studies suggest that genetic and/or environmental factors common to the families are more important than auto aeroallergen sensitization in the pathogenesis in asthma and allergy in "westernized" Asia. (See Lau Y L, Karlberg J, Yeung C Y. Prevalence of and factors associated with childhood asthma in Hong Kong. Acta Paediatrica 1995;84(7): 820–2.) In Istanbul, atopic family history, food allergy, eczema, frequent otitis media, and sinus attacks were found to be of significance in asthma's presence (22). When 1,500 lung experts met in Bangkok, Thailand, on Nov. 25, 1998, they agreed that the breath-robbing disease is on the rise in many countries, especially among children, and that a westernized life style was a major risk factor.

The International Study of Asthma in Childhood (ISAAC) studied 463,801 children, aged 13 to 14 years, situated in 155 collaborating centers in 56 countries. (See Lewis, S. ISAAC—a hypothesis generator for asthma? The Lancet 1998;351:1220–1224; Asher M I, Keil U, Anderson H R, Beasley R, Crane J, Mrtinez F, Mitchell E A, Pearce N, Sibbald B, Stewart A W, Strachan D, Weiland S K, Williams H C. International study of asthma and allergies in childhood (ISAAC): rationale and methods. Eur Respir J 1995; 8:483–491; and Writing Group and Steering Committee. Worldwide variation in prevalence of symptoms of asthma, allergic rhinoconjunctivitis, and atopic eczema: ISAAC. The Lancet 1998;351:1225–32.) One finding of the study was that countries with the lowest asthma rates, including several Eastern European countries, Indonesia, Greece, China, Taiwan, Uzbekistan, India, and Ethiopia, also had the lowest prevalence of allergic conjunctive, rhinitis and atopic eczema.

ISAAC found that the highest prevalence for asthma symptoms was mainly in English speaking centers and mainly in Western countries. These findings raised the possibility that environmental factors relating to living conditions in these countries are important. By contrast with the asthma findings, the highest prevalence of allergic rhinitis symptoms were reported from different centers in the world. Several centers with the highest symptom prevalence were not represented among the countries with the highest asthma prevalence. ISACC suggests that the major risk factors for these related disorders may differ or may involve different latency periods and time trends.

Allergic rhinitis may be missed in children, if some of the classic symptoms or signs are missing or they have indolent infections. A further problem is that "eczema" in one set of countries may be brushed off as simple "dry skin" in others. Some children may have been taught to consider so-called "dry skin" as nothing to worry about, and certainly not eczema. Sociological conditioning in different cultures as to what is normal or not may play some part in ISMC's findings.

When self reported symptoms of more than one atopic disorder were taken in to account, the highest prevalence were again observed in English speaking, westernized countries. ISMC also found that remarkable differences, and widely different prevalence, occurred between centers with populations of similar ethnic origins in countries such as China, (including Taiwan and Hong Kong), India, Italy, and Ethiopia. Once again these phenomena may have multiple causes that could in part be explained by the influence of Western culture.

Eczema is seen throughout life with an age distribution similar to that of asthma. Investigators have drawn attention to a seeming, but not understandable relationship between these two entities. (See Daniels Se, Bhattacharrya S, James A, Leaves N I, Young A, Hill M R, Faux J, Ryan G F, Ie Souef P N, Lathrop G M. A genome-wide search for quantitative trait loci underlying asthma. Nature. Sep. 19, 1996. 383(6597)L247–50.) In rich "westernized" countries, both are increasing. Various topical corticosteroids and antihistamines are commonly used in treatment. As with asthma, systemic corticosteroids are limited to severe exacerbations. Usually oral corticosteroids clear the skin only briefly. Stopping their use usually results in a return of the dermatitis. As with sinusitis and asthma, systemic corticosteroids bring about amelioration, but not cure. The use and effects of corticosteroids in the three diseases is similar.

Sinusitis, like eczema and asthma, is considered an inflammatory disease, the prevalence of which is rising. Possibly, 14% of the population is affected. Antibiotics, decongestants, antihistamines, and surgery are often used in its treatment, while corticosteroids are used to control it. (See Horner W E, Helbling A, Salvaggio J E, Lehrer S B. Fungal allergens. Clin Microbiol Rev 1995;8(2):161–179.)

SUMMARY OF THE INVENTION

The present invention is based on the discovery that eczema, allergic rhinitis and asthma result as a progression of the same disease process. This illness often first manifests itself as a fungal disease of the skin, which can become complicated by bacterial infection (Stage I).

Stage II is the inhalation, infection and sensitization of the nasal passages by the skin infection setting up an "allergic rhinitis." As time passes and with only symptomatic treatment, the mixed infective process increasingly damages the upper airway system and a chronic sinusitis may occur.

Stage III is a spreading of the infection into the airways & lungs and its sensitization by the same infective process, resulting in inflammatory airways obstruction, chronicity and the development of a myriad of secondary changes in the respiratory system and body.

More specifically, there are two parts to Stage I of the syndrome. The skin develops a fungal infection, which is mistakenly called "dry skin" (Stage IA). In the second part of the first stage this fungal infection spreads, becomes noticeably infected with bacteria, and is called "eczema" (Stage IB). The presence of either can result in the development of allergic rhinitis (Stage II A) and/or sinusitis (Stage II B).

Mildew, a type of fungi, usually results in situations when a normally dry surface becomes chronically wet. If a person's skin becomes chronically wet, the result will be infestation with fungi. Many experience this between their fourth and fifth toes when they do not dry off properly on a continual basis. Water normally evaporates off the skin even when not dried off with a towel. However, when water collects between the toes where air cannot reach it well, thereby keeping this area chronically wet, a condition we call "athlete's foot" or tinea pedis may develop. It may be mistaken for "dry skin," but it is actually a dermaphytic fungal infection.

When various substances such as lotions, moisturizers, oils, ointments, Vaseline, cocoa butter, greases, skin softeners and many baby care products are put on the skin, they can make the skin wet for weeks causing mildew to form on it. Most people mistake the mildew for so-called "dry skin." Soon to be patients see the white, flaky mildew on their skin, and assume that the skin is "dry." This results in their applying more lotion, which results in more and more mildew. Gradually the deposits of mildew become more obvious in various areas of the body, such as the heels, elbows, kneecaps, finger-webs, cheeks and scalp. Medically, when skin becomes chronically wet and infected with fungus, it is called tinea corporis (tinea of the body), tinea capitis (head), tinea cruris (groin), tinea manuum (hands), and tinea barbae (face). Once tinea is established in a body area, it requires treatment with a systematic antifungal drug, like itraconazole or terbinafine to get rid of it. If the infection is not treated in its entirety and completely cured, it tends to reoccur.

Giving cortisone or its derivatives merely treats the symptoms, but does not cure the infection. As a result, the lesions live on, causing chronicity and gradual spread over the body, particularly, if the daily application of lotions and moisturizers continues. This disease is then called "eczema" (Stage 1B).

The inventor has treated numerous patients with "eczema" and discovered that a large majority of the patients are cured by the use of oral antifungals for a period of time and/or antibiotics, preferably a combination of an antifungal and antibiotic. An oral antihistamine may be also be administered to help control itch, particularly in the early weeks of treatment. A part of this treatment is a cessation of all application of emollients, such as lotions, moisturizers, and the like. In one embodiment, the invention is directed to a method for treating eczema comprising reducing the application of emollients and administering an antifungal and/or an antibiotic.

Stage II is the development of "allergic rhinitis" (Stage IIA), which can, overtime, develop into an associated chronic sinusitis (Stage IIB). Itching of the conjunctiva, nose and pharynx, episodic rhinorrhea, sneezing, with obstruction of the nasal passages occurs. An incidence rate of about 7% is seen in North America. It is most common in childhood and adolescence. Swelling of turbinates and mucous membranes with obstruction of the sinus ostia and Eustachian tubes can cause secondary infections of the sinuses and middle ear. Nasal polyps often arise concurrently with edema and/or infection within the sinuses and increase obstructive symptoms.

If a person has fungus growing on their upper torso, face and/or scalp, it is just a matter of time before it would be inhaled into the nose and upper airways. Since it will be inhaled onto a wet surface, it is likely to take hold, perhaps causing a primary infection, a sensitizing reaction or a further sensitization to the fungus or perhaps all three. What begins as rhinitis can cause secondary sinusitis.

A useful first step in the treatment of sinusitis is the endoscopic removal of polyps and inflammatory material to establish aeration and drainage of involved sinuses, followed by administration of an antifungal agents along with reduction of application of emollients.

More specifically, when sinusitis has been present for years, the inventor has noted that a fungal infection may be part of the process and can cause "peanut butter" like plugs. Within the sinuses there are strategic areas such as the meatus in the ethmoid complex that are narrow. If these become blocked, as happens in infections, then obstructive sinusitis occurs. A fungus infection in an already damp environment tends to chronicity, making it easy to see how a fungal infection could cause obstructive sinusitis, with its resultant pathology.

These "peanut butter like" plugs should be surgically removed, such as by camera-controlled laparoscopic sinus surgery. However, for fungal sinusitis to be properly cured, the further inhalation of fungus from outside the nasal passages and sinuses must stop, thereby requiring the reduction of application of emollients. Additionally, effective control of sinusitis can result in improvement of asthma.

Stage III is a spreading of the infection into the airways & lungs and its sensitization by the same infective process, resulting in "bronchitis"(Stage IIIA) and/or "asthma"(Stage IIIB). Clinically, chronic bronchitis is often an early part of the onset of reversible obstructive airways disease. In another embodiment, the invention is directed to a method of treating bronchitis and/or asthma. The method comprises administering an antifungal and/or an antibiotic for a period of time and reducing the administration of emollients over that period of time.

The methods of the present invention, which involve the reduction or cessation of the administration of emollients is consistent with the knowledge that, as the level of income rises and populations become more "westernized", atopy takes hold. Specifically, as disposable income increases, the sale of "luxury" items, including perfumes, shampoos, cosmetics and skin care preparations, increases. The poor in rural areas and less-developed countries cannot afford such items. Nor are such people subject to the propaganda and salesmanship of the cosmetic industry, glossy magazines, and television. Additionally, the theory of the invention tends to explain why parental asthma is a risk factor, since parents who put lotions and the like over their own skin tend to do it to their children.

In one embodiment, the invention is directed to a method for treating an atopic disorder in a patient. The method comprises administering to the patient an effective amount of at least one of an antifungal and an antibiotic over a period of time. The method further includes reducing over the period of time the application of emollients to the patient by at least about 50%, relative to the amount of application of emollients prior to treatment.

In another embodiment, the invention is directed to a method for treating asthma comprising administering to the patient an effective amount of an antifungal over a first period of time and administering to the patient an effective amount of an antibiotic over a second period of time. The method further comprises reducing the application over a third period of time of emollients to the patient by at least about 80%, relative to the amount of application of emollients prior to treatment.

DESCRIPTION OF THE DRAWINGS

These and other features of the advantages of the present invention will be better understood by reference to the following detailed description when considered in conjunction with the accompanying photographs wherein.

This application file contains at least one photograph executed in color. Copies of this patent application publication with color photographs will be provided upon request and payment of the necessary fee.

DETAILED DESCRIPTION

Figure 1A:
FIG. 1A is a photograph showing Patient A (Example 6) prior to treatment.

In accordance with the methods of the invention, the administration of emollients is reduced by at least about 50%, more preferably at least about 80%, still more preferably at least about 90%, even more preferably at least about 95%, relative to the amount of application of emollients prior to treatment. In a particularly preferred embodiment, the administration of emollients is ceased altogether. As used herein, the term "emollients" includes lotions; creams; moisturizers; oils; ointments; cocoa butter; greases; skin softeners; soaps, shampoos, sunblocks, cosmetics and other products containing lotions, moisturizers or the like; products containing "slip" (a binder that allows pigment to slide across the skin); and any other product that softens the skin or soothes irritation in the skin. The period of time over which the administration of emollients is reduced or ceased is preferably at least about 1 month, more preferably at least about 2 months, still more preferably at least about 3 months, even more preferably at least about 6 months, yet more preferably at least about 1 year. The reduction or cessation of the administration of emollients is preferably continued for as long as possible to minimize the possible recurrence of the atopic disorder.

Suitable antifungals for use in connection with the invention include griseofulvin (such as FULVICIN, commercially available from Schering Corporation, Kenilworth, N.J.); ketoconazole (such as NIZORAL tables, commercially available from Janssen Pharmaceutica Inc., Titusville, N.J.); itraconazole (such as SPORANOX, commercially available from Janssen Pharmaceutica Inc.); and fluconazole (such as DIFLUCAN, commercially available from Pfizer Inc., New York, N.Y.). Particularly preferred anti-fungals are fungicidals, such as terbinafine (sold under the name LAMISIL by Novartis Pharmaceuticals Corporation, East Hanover, N.J.) naftifine, butemaifine, and amorolifine. The antifungal is preferably administered over a period of time of at least about 1 month, more preferably at least about 2 months, still more preferably at least about 3 months. Preferably the antifungal is administered to the patient in a dose ranging from about 10 mg to about 2000 mg per day, more preferably from about 250 mg to about 1000 mg per day.

Culture and sensitivity of the underlying lesion should determine the antibiotic. Suitable antibiotics for use in connection with the present invention include ciprofloxacin (such as CIPRO, commercially available from Bayer Corporation, West Haven, Conn.); trovafloxacin mesylate (such as TROVAN, commercially available from Pfizer Inc.); clavulanate potassium, amoxicillin and combinations thereof (such as AUGMENTIN, commercially available from SmithKline Beechm Pharmaceuticals, Philadelphia, Pa.); levofloxacin (such as LEVAQUIN, commercially available from Ortho-McNeil Pharmaceuticals, Raritan, N.J.); cefuroxime (such as CEFIN, commercially available from Glaxo Wellcome, Research Triangle Park, N.C.); clarithromycin (such as BIAXIN, commercially available from Abbott Laboratories, North Chicago, Ill.); tobramycin (such as NEBCIN, commercially available from Eli Lilly, Indianapolis, Ind.); azithromycin (such as ZITHROMAX, commercially available from Pfizer, New York, N.Y.); cephalexin; cefixime; cefpodoxime proxetil; flurconazole; trimethoprim; and sulfamethaxazole. The antibiotic is preferably administered over a period of time of at least about 1 month, more preferably at least about 2 months, still more preferably at least about 3 months. If both an antifungal and an antibiotic are administered, the antibiotic is preferably administered over a period of time concurrent, at least in part, with the period of time over which the antifungal is administered. Preferably the antibiotic is administered to the patient in a dose ranging from about 10 mg to about 2000 mg per day, more preferably from about 250 mg to about 1000 mg per day.

EXAMPLES

The following examples describe case studies showing the effect of application of an emollient and the reduction thereof on atopic disorders.

Example 1

A male, 33 year old patient recalled his mother putting lotion on his skin every day until the age of ten, at which time he had terrible asthma. His parents separated and he went to live with his father. His father put no lotion on him and over a period of time his asthma disappeared. Now in his 30's, the patient lives with his girlfriend who insists on putting lotion on his skin at every given opportunity. He now shows mildew on his elbows and knees and states that his sinuses are really "playing-up." He is starting to have asthma attacks once again.

Example 2

A male, 30 year old patient related that his mother put lotion on him everyday as a child, and he was continually being taken to the emergency room. At the age of seven or eight, his mother stopped putting lotions on him and at the age of approximately 14, his asthma had gone away. When he started dating girls at 17 or 18 years of age, he started putting lotion on his skin again, and has had asthma ever since.

Example 3

A female, 38 year old patient indicated that her mother and her aunts all used lotion everyday and all had asthma.

She could never remember a time in her life when her mother did not put lotion on her skin, a habit which she took over as she got older. She has four children, three of which she "lotioned-up" daily with great vigor. These three children developed asthma. The only time she had a remission at all from her illness was when she was a young teenager and during her third pregnancy, for reasons she did not understand. At the time of first consultation, she required four breathing treatments daily, with one occurring during the night. Her peak flows were in the range of 80. She was never without inhalers. She was attracted by the idea of giving up lotion altogether to save money and see what would happen. This patient did not take any antibiotics or antifungal medication. Within weeks, her "ash" was falling off her skin and after six weeks, she went into her first remission in 14 years. Peak flows went from 80 to 350. She needed no more breathing treatments and rarely used an inhaler.

Example 4

A male, 30 year old patient had been free of asthma and rhinitis all of his life, when he started putting lotions on his face on a daily basis for months. He developed asthma about one year later. He stopped putting lotion on his face, and his asthma nearly went away. However, he still had his sinusitis. At rest his peak flow was 435, but after albuterol and beclomethasone inhalers, it was a normal 570.

Example 5

A female, 26 year old patient told of suffering from severe sinusitis and then asthma for months, yet physical examination showed no signs of tinea corporis. She stated she never put any lotions, etc. anywhere on her skin. When asked why her hair was so closely cropped, she related that she developed terrible psoriasis on her scalp when she switched her hair shampoo 2 years previously. Examination showed she really suffered from tinea capitis.

Example 6

Eight patients that skin fungal conditions were treated by administration of griseovulvin (500 mg, twice a day) and an appropriate antibiotic chosen by the culture and sensitivity. Most patients received an antihistamine for the first ten days to control itch. The patients ceased the use of lotions and other emollients, as well as the use of local and systemic corticosteroids. The results were impressive, as described below.

Figure 1B:
FIG. 1B is a photograph showing Patient A after treatment.

Patient A—As shown in FIG. 1A, Patient A had "dry skin" syndrome fostered by years of skin care products. FIG. 1B, shows Patient A after 35 days of treatment. Although some white fungus can still be observed, the appearance of "dry skin" cleared up considerably.

Figure 2A:
FIG. 2A is a photograph showing Patient B (Example 6) prior to treatment.
Figure 2B:
FIG. 2B is a photograph showing Patient B after treatment.

Patient B—As shown in FIG. 2A, Patient B was covered in fungus, and Patient B had a bacterial infection. FIG. 2B shows Patient B one week later, with the fungus having improved dramatically.

Figure 3A:
FIG. 3A is a photograph showing Patient C (Example 6) prior to treatment.
Figure 3B:
FIG. 3B is a photograph showing Patient C after treatment.

Patient C—Patient C had spent almost 24 years visiting dermatologists in an attempt to clear his skin condition, as shown in FIG. 3A. Upon culturing the fungus, we discovered it to be proteus. FIG. 3B shows Patient C after treatment, with the fungus significantly improved.

Figure 4A:
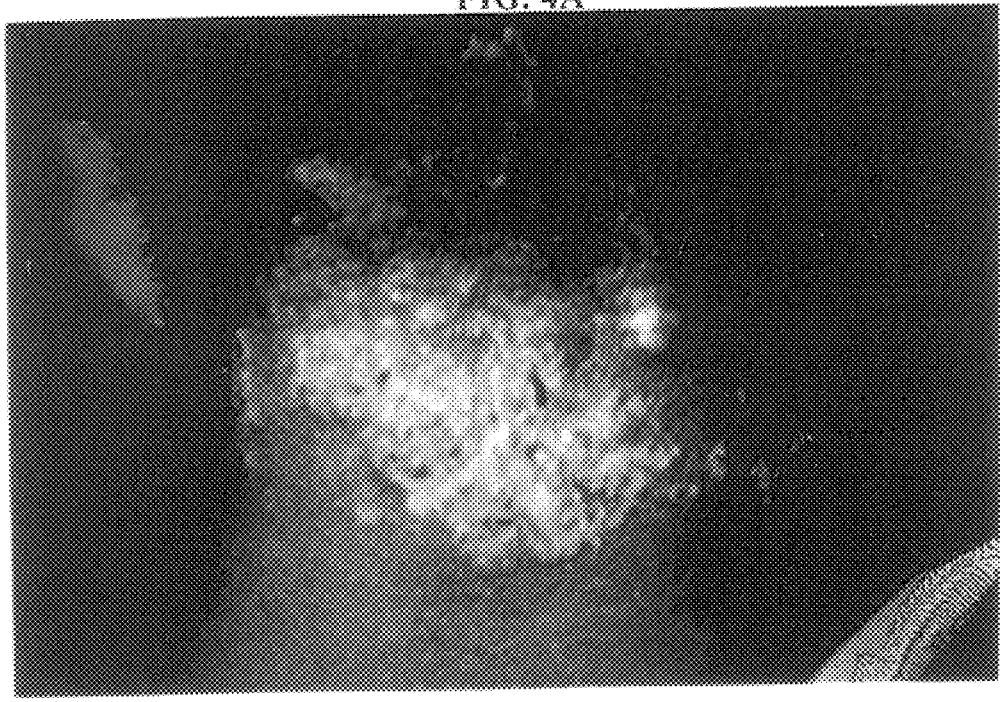
FIG. 4A is a photograph showing Patient D (Example 6) prior to treatment.
Figure 4B:
FIG. 4B is a photograph showing Patient D after treatment.

Patient D—FIG. 4A shows the fungus on the back of Patient D's neck. This is believed to be a result of the use of shampoo and other hair products containing moisturizer. The products ran off the back of the patient's hair and stayed on his neck, creating a fungus growth followed by a bacterial infection. FIG. 4B shows Patient D after seven weeks, with the fungus growth significantly diminished.

Figure 5A:
FIG. 5A is a photograph showing Patient E (Example 6) prior to treatment.
Figure 5B:
FIG. 5B is a photograph showing Patient E after treatment.

Patient E—Prior to treatment, Patient E, an African American, was while over almost all of his body. FIG. 5A shows only Patient E's knee area, although his arms, hands, back, abdomen and neck were also all while. He also had a very severe case of itching, and he was put on 100 mg of diphenhydramine four times a day to help control his itch. FIG. 5B shows Patient E in the sub-patella area after eleven weeks of treatment. The white skin shown in this photograph is actually scar tissue from years of scratching.

Figure 6A:
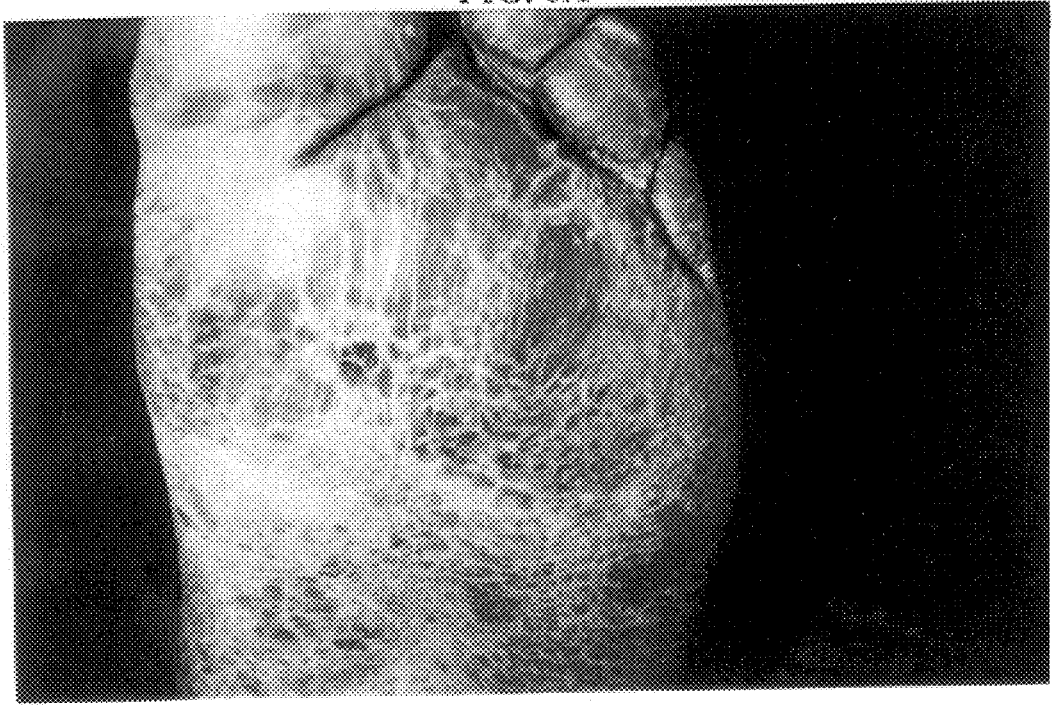
FIG. 6A is a photograph showing Patient F (Example 6) prior to treatment.
Figure 6B:
FIG. 6B is a photograph showing Patient F after treatment.

Patient F—Patient F had a severe fungal conduction, as shown in FIG. 6A, and had been treated with Lidex for twenty-eight years. After seven weeks of treatment, the fungas was improving and peeling off, as shown in FIG. 6B.

Figure 7A:
FIG. 7A is a photograph showing Patient G (Example 6) prior to treatment.
Figure 7B:
FIG. 7B is a photograph showing Patient G after treatment.

Patient G—Patient G, shown in FIG. 7A, had the fungal infection tinea barbae, but had previously only been treated for acne. FIG. 7B shows Patient G after seven weeks, with the fungal infection significantly cleared, although scars still remain.

Figure 8A:
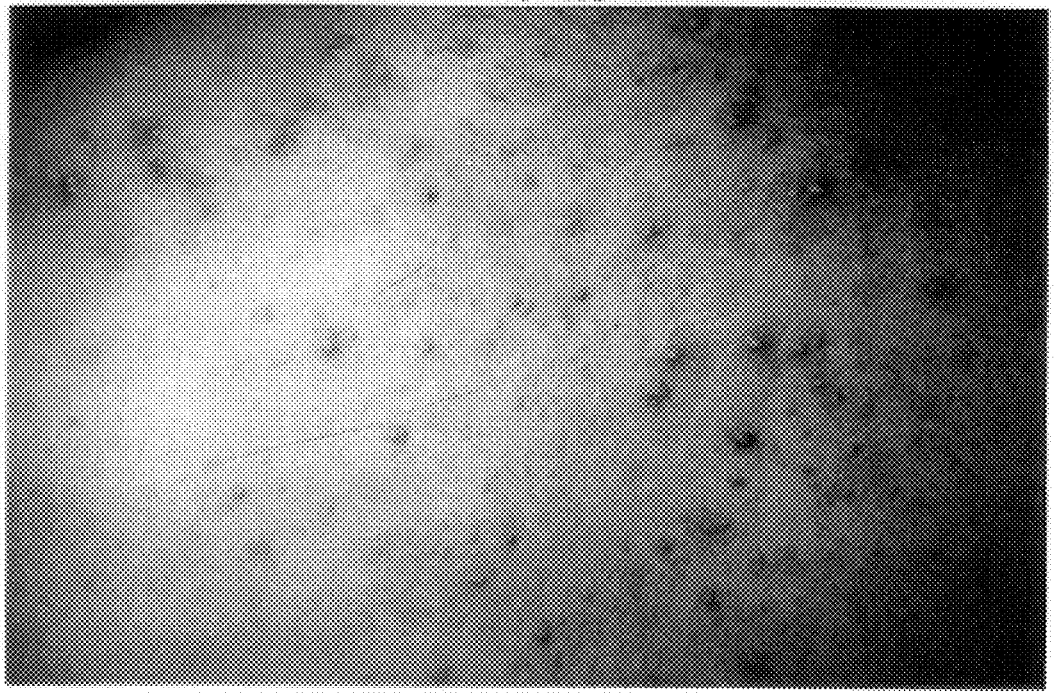
FIG. 8A is a photograph showing Patient H (Example 6) prior to treatment.
Figure 8B:
FIG. 8B is a photograph showing Patient H after treatment.

Patient H—Patient H, shown in FIG. 8A, had hair follicles that became infected byfungus. After nine weeks of treatment, his skin was dramatically improved, as shown in FIG. 8B.

Example 7

Thirty-two randomly-selected successive asthma patients were treated by administration of griseovulvin (500 mg, twice a day) and ciprofloxacin (CIPRO, one double-strength tablet twice a day). All of the patients ceased use of all lotions and other emollients during treatment.

For each patient, peak flow measurements were taken using a peak flow meter, where a higher peak value typically indicates improved breathing. Counts were taken of eosinophils, which secrete chemical mediators that can cause bronchoconstriction in asthma. Counts were also taken of IgE antibodies. The use of an inhaler by each patient was also monitored.

Patient 1 (age 44) had been on Prednisone until 6 weeks before treatment.

| Day | Peak Flow | Eosinophils | IgE antibodies | Inhaler use per day |
| --- | --- | --- | --- | --- |
| 1 | 240 | 270 | 260 | 1 |
| 14 | 360 | | | 1 |
| 19 | 620 | | | 0 |

Patient 2 (age 36)

| Day | Peak Flow | Eosinophils | IgE antibodies | Inhaler use per day |
| --- | --- | --- | --- | --- |
| 1 | 450 | | | 2 |
| 14 | 600 | | | 0 |
| 19 | 620 | | | 0 |

Patient 3 (age 54) had been on prednisone for many years prior to treatment and had undergone multiple hospitalizations for her asthma. During treatment, her dosage of prednisone was slowly decreased.

Patient 4 (age 45)

| Day | Daily Dose of Prednisone (mg) | Peak Flow | Eosinophils | IgE antibodies | Inhaler use per day |
|---|---|---|---|---|---|
| 1  | 40  | 370 |  |  | 6–8 |
| 13 | 5   | 240 |  |  | 5 |
| 20 | 7.5 | 400 |  |  | 3 |
| 26 | 3.3 | 380 |  |  | 2 |
| 32 | 2.5 | 450 |  |  | 1 |

Patient 5 (age 23)

| Day | Peak Flow | Eosinophils | IgE antibodies | Inhaler use per day |
|---|---|---|---|---|
| 1  | 550 | 322 | 214 | 1 |
| 8  | 630 |  |  | 0 |
| 15 | 650 |  |  | 0 |

| Day | Peak Flow | Eosinophils | IgE antibodies | Inhaler use per day |
|---|---|---|---|---|
| 1 | 160 |  |  | 3 |
| 4 | 320 |  |  | 2 |

Patient 6 (age 63) had been on Prednisone for most of the fifteen years preceding treatment, had previously been in the intensive care unit, and had been hospitalized over sixty times for asthma prior to treatment.

| Day | Peak Flow | Eosinophils | IgE antibodies | Inhaler use per day |
|---|---|---|---|---|
| 1  | 230 | 912 | 530 | 6 |
| 21 | 450 | 561 | 764 | 4 |
| 25 | 530 | 179 |     | 3 |
| 32 | 750 |     | 176 | 3 |
| 43 | 710 |     |     | 2 |

Patient 7 (age 50) had been in the intensive care unit four times for asthma prior to treatment.

| Day | Peak Flow | Eosinophils | IgE antibodies | Inhaler use per day |
|---|---|---|---|---|
| 1  | 340 | 256 |  | 2 |
| 7  | 440 |     |  | 1 |
| 14 | 500 |     |  | 1 |

Patient 8 (age 21)

| Day | Peak Flow | Eosinophils | IgE antibodies | Inhaler use per day |
|---|---|---|---|---|
| 1 | 455 |  |  | 3 |
| 8 | 540 |  |  | 0 |

Patient 9 (age 50) had been in the intensive care unit four times for asthma prior to treatment

| Day | Peak Flow | Eosinophils | IgE antibodies | Inhaler use per day |
|---|---|---|---|---|
| 1  | 340 | 256 | 65 | 2 |
| 7  | 440 |     |    | 1 |
| 14 | 500 | 85  |    | 1 |

Patient 10 (age 21)

| Day | Peak Flow | Eosinophils | IgE antibodies | Inhaler use per day |
|---|---|---|---|---|
| 1 | 349 | 352 |  | 3 |
| 8 | 550 |     |  | 1 |

Patient 11 (age 42) had been in the emergency room three times and the hospital twice for asthma prior to treatment.

| Day | Peak Flow | Eosinophils | IgE antibodies | Inhaler use per day |
|---|---|---|---|---|
| 1  | 480 | 70 | 140 | 3 |
| 16 | 430 |    |     | 0 |

Patient 12 (age 39) had been in the intensive care unit and hospital prior to treatment.

| Day | Peak Flow | Eosinophils | IgE antibodies | Inhaler use per day |
|---|---|---|---|---|
| 1  | 180 | 322 | 169 | 2 |
| 14 | 460 |     |     | 0 |

Patient 13 (age 30) had been in the emergency room five times for asthma prior to treatment.

| Day | Peak Flow | Eosinophils | IgE antibodies | Inhaler use per day |
|---|---|---|---|---|
| 1  | 250 | 246 | 285 | 2 |
| 21 | 480 |     |     | 0 |

Patient 14 (age 58)

| Day | Peak Flow | Eosinophils | IgE antibodies | Inhaler use per day |
|---|---|---|---|---|
| 1   | 485 |  |  | 8 |
| 30  | 540 |  |  |   |
| 50  | 580 |  |  |   |
| 90  | 570 |  |  |   |
| 110 | 620 |  |  |   |
| 130 | 635 |  |  | 0 |
| 140 | 620 |  |  |   |
| 150 | 640 |  |  |   |
| 170 | 620 |  |  |   |

-continued

| Day | Peak Flow | Eosinophils | IgE antibodies | Inhaler use per day |
|---|---|---|---|---|
| 330 | 650 | | | |
| 370 | 640 | | | 0 |

Patient 15 (age 27) had polydermaphytis and nasal and perioral rash with green sputum.

| Day | Peak Flow | Eosinophils | IgE antibodies | Inhaler use per day |
|---|---|---|---|---|
| 1 | 360 | 432 | 31 | 0 |
| 9 | 480 | | | 0 |

Patient 16 (age 67) had forty emergency room visits and ten hospitalization for asthma prior to treatment.

| Day | Peak Flow | Eosinophils | IgE antibodies | Inhaler use per day |
|---|---|---|---|---|
| 1 | 250 | 767 | 750 | 12 |
| 6 | 270 | | | 1 |
| 9 | 320 | 845 | 611 | 1 |
| 12 | 400 | | | 1 |

Patient 17 (age 23) has multiple emergency room visits prior to treatment. On day 30 of treatment, Patient 11 walked in and announced, "I am cured." Patient 11's age and size matched a mean peak flow of 590.

| Day | Peak Flow | Eosinophils | IgE antibodies | Inhaler use per day |
|---|---|---|---|---|
| 1 | 280 | 477 | 161 | 4 |
| 30 | 770 | 301 | 98 | 0 |
| 44 | 750 | | | 0 |

Patient 18 (age 45) has been in the intensive care unit three times for asthma prior to treatment.

| Day | Peak Flow | Eosinophils | IgE antibodies | Inhaler use per day |
|---|---|---|---|---|
| 1 | 370 | 141 | | 3 |
| 7 | 420 | | | 1 |

Patient 19 (age 24) had made nearly two hundred emergency room visits for asthma prior to treatment.

| Day | Peak Flow | Eosinophils | IgE antibodies | Inhaler use per day |
|---|---|---|---|---|
| 1 | 280 | 447 | | 5 |
| 8 | 460 | | | 4 |

Patient 20 (age 25) had been in the emergency room twice and the intensive care unit once for asthma prior to treatment.

| Day | Peak Flow | Eosinophils | IgE antibodies | Inhaler use per day |
|---|---|---|---|---|
| 1 | 310 | 128 | 108 | 3 |
| 14 | 500 | | | 2 |

Patient 21 (age 21)

| Day | Peak Flow | Eosinophils | IgE antibodies | Inhaler use per day |
|---|---|---|---|---|
| 1 | 440 | 341 | 115 | 2 |
| 7 | 530 | | | 1 |
| 14 | 540 | | | 0 |

Patient 22 (age 38) had five emergency room visits for asthma prior to treatment.

| Day | Peak Flow | Eosinophils | IgE antibodies | Inhaler use per day |
|---|---|---|---|---|
| 1 | 250 | 246 | 285 | 2 |
| 27 | 480 | | | 1 |

Patient 23 (age 23) had been in the emergency room twice and the intensive care unit once for asthma prior to treatment.

| Day | Peak Flow | Eosinophils | IgE antibodies | Inhaler use per day |
|---|---|---|---|---|
| 1 | 380 | | 3350 | 5 |
| 3 | 470 | | | 3 |
| 6 | 530 | | | 1 |

Patient 24 (age 36) had been hospitalized twice and in the intensive care unit once for asthma prior to treatment.

| Day | Peak Flow | Eosinophils | IgE antibodies | Inhaler use per day |
|---|---|---|---|---|
| 1 | 280 | 186 | 501 | 2 |
| 7 | 500 | | | 1 |
| 14 | 620 | 405 | 555 | 0 |

Patient 25 (age 18) had made an emergency room visit for asthma prior to treatment.

| Day | Peak Flow | Eosinophils | IgE antibodies | Inhaler use per day |
|---|---|---|---|---|
| 1 | 450 | | | 2 |
| 8 | 660 | | | 1 |

Patient 26 (age 27) had made three emergency room visits for asthma prior to treatment.

| Day | Peak Flow | Eosinophils | IgE antibodies | Inhaler use per day |
|---|---|---|---|---|
| 1 | 270 | 192 | 220 | 4 |
| 7 | 430 | | | 2 |

Patient 27 (age 32)

| Day | Peak Flow | Eosinophils | IgE antibodies | Inhaler use per day |
|---|---|---|---|---|
| 1 | 550 | | | 4 |
| 7 | 590 | 282 | 230 | 2 |
| 14 | 780 | 565 | 202 | 0 |
| 25 | 760 | | | 0 |

Patient 28 (age 48) had made five emergency room visits and been in the intensive care unit three times for asthma prior to treatment.

| Day | Peak Flow | Eosinophils | IgE antibodies | Inhaler use per day |
|---|---|---|---|---|
| 1 | 230 | 154 | | 1 |
| 8 | 290 | | | 0 |

Patient 29 (age 28) had multiple hospitalizations for asthma prior to treatment.

| Day | Peak Flow | Eosinophils | IgE antibodies | Inhaler use per day |
|---|---|---|---|---|
| 1 | 460 | | | 2 |
| 7 | 500 | | | 1 |

Patient 30 (age 28)

| Day | Peak Flow | Eosinophils | IgE antibodies | Inhaler use per day |
|---|---|---|---|---|
| 1 | 420 | 114 | 18 | 4 |
| 7 | 550 | | | 3 |
| 14 | 550 | | | 3 |
| 21 | 560 | | 13 | 2 |

Patient 31 (age 21) had been in the emergency room nearly fifty times and hospitalized nearly eighty times for asthma prior to treatment.

| Day | Peak Flow | Eosinophils | IgE antibodies | Inhaler use per day |
|---|---|---|---|---|
| 1 | 350 | 352 | 104 | 4 |
| 16 | 610 | 200 | | 2 |

Patient 32 (age 21) had been in the emergency room five times and hospitalized ten times for asthma prior to treatment.

| Day | Peak Flow | Eosinophils | IgE antibodies | Inhaler use per day |
|---|---|---|---|---|
| 1 | 380 | 202 | 39 | 4 |
| 14 | 540 | | | 0 |

What is claimed is:

1. A method for treating asthma in a patient, comprising:
    administering to the patient an effective amount of at least one of an antifungal and an antibiotic; and
    reducing the application of emollients to the patient by at least about 50%, relative to the amount of application of emollients prior to treatment wherein the emollients are selected from the group consisting of lotions, creams, moisturizers, oils, ointments, cocoa butter, greases, skin softeners, soaps containing lotions or moisturizers, shampoos containing lotions or moisturizers, sunblocks containing lotions or moisturizers, cosmetics containing lotions or moisturizers, and products containing slip.
2. A method according to claim 1, wherein the antifungal is a fungicidal.
3. A method according to claim 1, wherein the antifungal is terbinafine.
4. A method according to claim 1, wherein the antifungal is an oral antifungal.
5. A method according to claim 1, comprising administering both an antifungal and an antibiotic.
6. A method according to claim 1, wherein the at least one of an antifungal and an antibiotic is administered over a period of time of at least about 1 month.
7. A method according to claim 1, wherein the at least one of an antifungal and an antibiotic is administered over a period of time of at least about 2 months.
8. A method according to claim 1, wherein the at least one of an antifungal and an antibiotic is administered over a period of time of at least about 3 months.
9. A method according to claim 1, wherein the application of emollients to the patient is reduced by at least about 80%, relative to the amount of application of emollients prior to treatment.
10. A method according to claim 1, wherein the application of emollients to the patient is reduced by at least about 90%, relative to the amount of application of emollients prior to treatment.
11. A method according to claim 1, wherein the application of emollients to the patient is reduced by at least about 95%, relative to the amount of application of emollients prior to treatment.
12. A method according to claim 1, wherein the application of emollients to the patient is ceased.
13. A method according to claim 1, wherein the administration is over a first period of time of at least about 1 month, and the reduction is over a second period of time of at least about 6 months.
14. A method according to claim 13, wherein the first period of time is at least about 3 months.
15. A method according to claim 14, wherein the second period of time is at least about 1 year.
16. A method according to claim 1, further comprising administering an antihistamine.

17. A method for treating asthma in a patient, comprising:
administering to the patient an effective amount of an antifungal;
administering to the patient an effective amount of an antibiotic; and
reducing the application of emollients to the patient by at least about 80%, relative to the amount of application of emollients prior to treatment, wherein the emollients are selected from the group consisting of lotions, creams, moisturizers, oils, ointments, cocoa butter, greases, skin softeners, soaps containing lotions or moisturizers, shampoos containing lotions or moisturizers, sunblocks containing lotions or moisturizers, cosmetics containing lotions or moisturizers, and products containing slip.

18. A method according to claim 17, wherein the antifungal is administered over a period of time of at least about 2 months.

19. A method according to claim 17, wherein the antifungal is administered over a period of time of at least about 3 months.

20. A method according to claim 17, wherein the antibiotic is administered over a period of time of at least about 2 months.

21. A method according to claim 17, wherein the antibiotic is administered over a period of time of at least about 3 months.

22. A method according to claim 17, wherein the third period of time is at least about 3 months.

23. A method according to claim 17, wherein the third period of time is at least about 6 months.

24. A method according to claim 17, wherein the reduction of emollients occurs simultaneously with at least part of the period of time over which the antifungal is administered.

25. A method according to claim 17, wherein the antifungal is a fungicidal.

26. A method according to claim 17, wherein the antifungal is terbinofine.

27. A method according to claim 17, wherein the application of emollients to the patient is reduced by at least about 95%, relative to the amount of application of emollients prior to treatment.

28. A method according to claim 17, wherein the application of emollients to the patient is ceased.

29. A method according to claim 17, further comprising administering an antihistamine.

30. A method according to claim 29, wherein the administration of the antihistamine is provided over a period that overlaps, at least in part, with the administration of the antibiotic.

31. A method for treating asthma in a patient, comprising:
administering to the patient an effective amount of at least one of an antifungal and an antibiotic; and
simultaneously reducing the application of emollients to the patient by at least about 50%, relative to the amount of application of emollients prior to treatment, wherein the emollients are selected from the group consisting of lotions, creams, moisturizers, oils, ointments, cocoa butter, greases, skin softeners, soaps containing lotions or moisturizers, shampoos containing lotions or moisturizers, sunblocks containing lotions or moisturizers, cosmetics containing lotions or moisturizers, and products containing slip.

32. A method according to claim 31, comprising administering both an antifungal and an antibiotic.

33. A method according to claim 32, wherein the antifungal is a fungicidal.

34. A method according to claim 32, wherein the antifungal is terbinafine.

35. A method according to claim 32, wherein the antifungal and antibiotic are administered over a period of time of at least about 1 month.

36. A method according to claim 32, wherein the antifungal and antibiotic are administered over a period of time of at least about 2 months.

37. A method according to claim 32, wherein the antifungal and antibiotic are administered over a period of time of at least about 3 months.

38. A method according to claim 31, wherein the application of emollients to the patient is reduced by at least about 80%, relative to the amount of application of emollients prior to treatment.

39. A method according to claim 31, wherein the application of emollients to the patient is ceased.

40. A method according to claim 31, further comprising administering an antihistamine.

41. A method according to claim 6, wherein the application of emollients is reduced over a period of time of at least about 1 month.

42. A method according to claim 7, wherein the application of emollients is reduced over a period or time of at least about 2 months.

43. A method according to claim 8, wherein the application of emollients is reduced over a period of time of at least about 3 months.

44. A method according to claim 17, wherein:
the antifungal is administered over a period of time of at least about 1 month;
the antibiotic is administered over a period of time of at least about 1 month; and
the application of emollients is reduced over a period of time of at least about 1 month.

45. A method according to claim 17, wherein:
the antifungal is administered over a period of time of at least about 2 months;
the antibiotic is administered over a period of time of at least about 2 months; and
the application of emollients is reduced over a period of time of at least about 2 months.

46. A method according to claim 17, wherein;
the antifungal is administered over a period of time of at least about 3 months;
the antibiotic is administered over a period of time of at least about 3 months; and
the application of emollients is reduced over a period of time of at least about 3 months.

* * * * *